United States Patent

Marschner et al.

Patent Number: 5,962,730
Date of Patent: Oct. 5, 1999

[54] AROMATIC SULPHONYL COMPOUNDS HAVING AN ADDITIONAL THIOETHER, SULPHOXIDE OR SULPHONYL GROUP

[75] Inventors: Claus Marschner, Speyer; Manfred Patsch, Wachenheim, both of Germany

[73] Assignee: BASF Aktiengesellschaft, Ludwigshafen, Germany

[21] Appl. No.: 08/981,497

[22] PCT Filed: Jul. 4, 1996

[86] PCT No.: PCT/EP96/02929

§ 371 Date: Jan. 9, 1998

§ 102(e) Date: Jan. 9, 1998

[87] PCT Pub. No.: WO97/03955

PCT Pub. Date: Feb. 6, 1997

[30] Foreign Application Priority Data

Jul. 14, 1995 [DE] Germany .......................... 195 25 679

[51] Int. Cl.⁶ ................................................ C07C 305/04
[52] U.S. Cl. ................................. 562/42; 562/44; 562/45; 562/73; 558/411; 564/305; 568/27; 568/28; 568/29; 546/347
[58] Field of Search ................... 562/42, 44, 45, 562/73; 558/411; 564/305; 546/347; 568/27, 28, 29

[56] References Cited

U.S. PATENT DOCUMENTS 2,098,759  11/1937  Reppe .

OTHER PUBLICATIONS

Beilstein ref no 3137596 preparation found in J chem Soc 2433,2440, Ford–Moore, 1949.

*Primary Examiner*—Gary Geist
*Assistant Examiner*—Jean F. Volleim
*Attorney, Agent, or Firm*—Oblon, Spivak, McClelland, Maier & Neustadt, P.C.

[57] ABSTRACT

Sulfonyl compounds have the formula

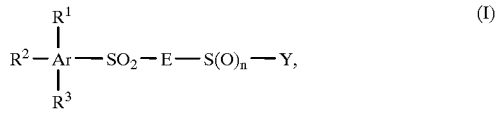

where n is 0, 1 or 2,

Y is vinyl or a radical of the formula $C_2H_4Q$, where Q is hydroxyl or an alkali-detachable group, E is $C_3$–$C_6$-alkylene with or without interruption by 1 or 2 oxygen atoms in ether function, Ar is the radical of benzene or naphthalene, and $R^1$, $R^2$ and $R^3$ are each hydrogen, unsubstituted or substituted $C_1$–$C_6$-alkyl, $C_1$–$C_6$-alkoxy, hydroxyl, halogen, nitro, amino, hydroxysulfonyl, carboxyl, carbamoyl, sulfamoyl, cyano or a radical of the formula $(NH-)_m(CH_2-)_qSO_2-Y$, where m is 0 or 1, q is 0, 2 or 3, and Y is as defined above.

8 Claims, No Drawings

AROMATIC SULPHONYL COMPOUNDS HAVING AN ADDITIONAL THIOETHER, SULPHOXIDE OR SULPHONYL GROUP

This is the national stage of PCT/EP96/02929 filed Jul. 4, 1996.

The present invention relates to novel sulfonyl compounds of the formula I

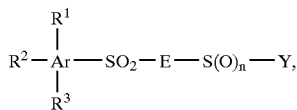

where n is 0, 1 or 2,

Y is vinyl or a radical of the formula $C_2H_4Q$, where Q is hydroxyl or an alkali-detachable group, E is $C_3$–$C_6$-alkylene with or without interruption by 1 or 2 oxygen atoms in ether-function, Ar is the radical of benzene or naphthalene, and $R^1$, $R^2$ and $R^3$ are independently of each other hydrogen, $C_1C_6$-alkyl with or without amino or $C_1$–$C_4$-alkanoylamino substitutions $C_1$–$C_6$-alkoxy, hydroxyl, halogen, nitro, amino, $C_1$–$C_4$-alkanoylamino, mono- or di($C_1$–$C_6$-alkyl)amino, hydroxysulfonyl, carboxyl carbamoyl, mono- or di($C_1$–$C_6$-alkyl)carbamoyl, sulfamoyl, mono- or di($C_1$–$C_6$-alkyl)sulfamoyl, cyano or a radical of the formula $(NH—)_m(CH_2—)_qSO_2—Y$, where m is 0 or 1, q is 0, 2 or 3, and Y is as defined above.

It is an object of the present invention to provide novel aromatic sulfonyl compounds having an additional thioether, sulfoxide or sulfonyl group in the molecule. The novel compounds shall be easy to obtain and advantageously useful as intermediates for dyes.

We have found that this object is achieved by the above-defined aromatic sulfonyl compounds of the formula I.

Any alkyl or alkylene appearing in the formulae recited herein may be straight-chain or branched $R^1$, $R^2$ and $R^3$ are each, for example, methyl, ethyl, propyl, isopropyl, butyl, isobutyl, sec-butyl, tert-butyl, pentyl, isopentyl, neopentyl, tert-pentyl, hexyl, 2-methylpentyl, aminomethyl, 2-aminoethyl, 2- or 3-aminopropyl, 2- or 4-aminobutyl, 5-aminopentyl, 6-aminohexyl, formylaminomethyl, 2-formylaminoethyl, 2- or 3-formylaminopropyl, 2- or 4-formylaminobutyl, 5-formylaminopentyl, 6-formylaminohexyl, acetylaminomethyl, 2-acetylaminoethyl, 2- or 3-acetylaminopropyl, 2- or 4-acetylaminobutyl, 5-acetylaminopentyl, 6-acetylaminohexyl, methoxy, ethoxy, propoxy, isopropoxy, butoxy, isobutoxy, sec-butoxy, pentyloxy, isopentyloxy, neopentyloxy, tert-pentyloxy, hexyloxy, fluorine, chlorine, bromine, mono- or dimethylamino, mono- or diethylamino, mono- or dipropylamino, mono- or diisopropylamino, mono- or dibutylamino, mono- or dipentylamino, mono- or dihexylamino, mono- or dimethylcarbamoyl, mono- or diethylcarbamoyl, mono- or dipropylcarbamoyl, mono- or dibutylcarbamoyl, mono- or dipentylcarbamoyl, mono- or dihexylcarbamoyl, mono- or dimethylsulfamoyl, mono- or diethylsulfamoyl, mono- or dipropylsulfamoyl, mono- or dibutylsulfamoyl, mono- or dipentylsulfamoyl, mono- or dihexylsulfamoyl, formylamino, acetylamino, propionylamino, butyrylamino or isobutyrylamino.

E is for example $(CH_2)_3$, $(CH_2)_4$, $(CH_2)_5$, $(CH_2)_6$, $CH(CH_3)CH_2$, $CH(CH_3)CH(CH_3)$, $(CH_2)_2O(CH_2)_2$, $(CH_2)_2O(CH_2)_3$, $(CH_2)_3O(CH_2)_3$ or $(CH_2)_2O(CH_2)_2O(CH_2)_2$.

Q is hydroxyl or an alkali-detachable group. Examples of such groups include chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, phenylsulfonyloxy, $C_1$–$C_4$-alkanoyloxy, di($C_1$–$C_4$-alkyl)amino or a radical of the formula

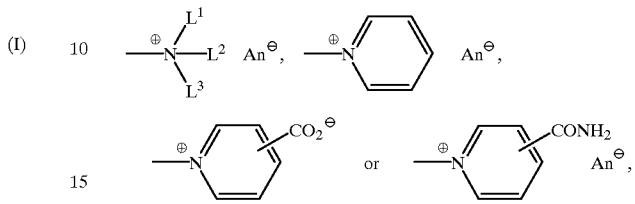

where $L^1$, $L^2$ and $L^3$ are independently of each other $C_1$–$C_4$-alkyl or benzyl and $An^\ominus$ is in each case one equivalent of an anion. Examples of suitable anions include fluoride, chloride, bromide, iodide, mono- di- or trichloroacetate, methanesulfonate, benzenesulfonate and 2- or 4-methylbenzenesulfonate.

Preference is given to sulfonyl compounds of the formula I where n is 0 or 2, in particular 2.

Preference is further given to sulfonyl compounds of the formula I where E is $C_3$- or $C_4$-alkylene, in particular $C_3$-alkylene.

Preference is further given to sulfonyl compounds of the formula I where Ar is the radical of benzene Preference is further given to sulfonyl compounds of the formula I where $R^1$ is $C_1$–$C_4$-alkyl with or without amino or $C_1$–$C_4$-alkanoylamino substitution, nitro, amino or $C_1$–$C_4$-alkanoylamino and $R^2$ and $R^3$ are independently of each other hydrogen, $C_1$–$C_4$-alkoxy, hydroxyl, halogen, hydroxysulfonyl or carboxyl.

Particular preference is given to sulfonyl compounds of the formula I where $R^1$ is $C_1$–$C_4$-alkyl with or without amino or $C_1$–$C_4$-alkanoylamino substitution, nitro, amino or $C_1$- or $C_2$-alkanoylamino, $R^2$ is hydrogen, $C_1$–$C_4$-alkoxy, hydroxyl, halogen, hydroxysulfonyl or carboxyl and $R^3$ is hydrogen or hydroxysulfonyl.

Of particular industrial interest are sulfonyl compounds of the formula Ia

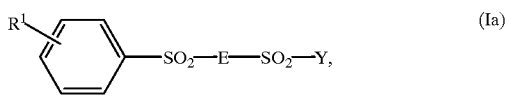

where

Y is vinyl, 2-sulfatoethyl, 2-chloroethyl or 2-acetyloxyethyl,

E is $C_3$- or $C_4$-alkylene, and $R^1$ is $C_1$–$C_4$-alkyl with or without amino or $C_1$- or $C_2$-alkanoylamino substitution, nitro, amino or $C_1$- or $C_2$-alkanoylamino.

The sulfonyl compounds of the formula I according to the present invention can be obtained by methods known per se. Advantageously, for example, an aromatic compound of the formula II

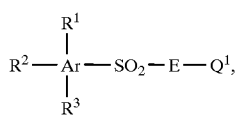

(II)

where E, Ar, $R^1$, $R^2$ and $R^3$ are each as defined above and $Q^1$ has the meanings of Q other than hydroxyl, is reacted with mercaptoethanol to form the hydroxyl compound of the formula Ib

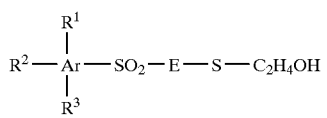

(Ib)

where E, Ar, $R^1$, $R^2$ and $R^3$ are each as defined above.

If desired, this hydroxyl compound can subsequently be oxidized, for example with hydrogen peroxide, to the sulfoxide (n=1 in the formula I) or sulfone (n=2 in the formula I) and, again if desired, the alkali-detachable group can be introduced subsequently, for example by esterification with sulfuric acid. However, it is also possible to introduce the alkali-detachable group into the hydroxyl compound of the formula Ib and only then to oxidize it, if desired.

The novel sulfonyl compounds of the formula I are useful intermediates for preparing reactive dyes.

The Examples which follow illustrate the invention.

EXAMPLE 1

173 g of 1-bromo-3-chloropropane were added dropwise at from 20 to 25° C. to a mixture of 200 g of 4-acetylaminobenzenesulfinic acid, 500 ml of N,N-dimethylformamide (DMF) and 152 g of potassium carbonate. The mixture was subsequently stirred at from 20 to 25° C. for 12 hours.

After the reaction had ended (TLC), the reaction mixture was poured onto 750 g of ice and subsequently stirred for 1 h. The precipitate was filtered off with suction, washed neutral with water and dried at 50° C. under reduced pressure, leaving 260 g of the compound of the formula

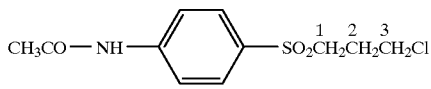

$^1$H-NMR (D$_6$-DMSO): δ=2.0 (m, 2H, 2-H), 2.1 (S, 3H, CH$_3$)

3.3 (t, 2H, 3-H)

3.7 (t, 2H, 1-H)

7.8 (brs, 4H, aromatic H) ppm.

$^{13}$C-NMR (D$_6$-DMSO): δ=24.1 (CH$_3$), 26.1 (C-2), 43.0 (C-3)

52.8 (C-1), 118.9, 128.9, 132.2

144.2 (aromatic C), 169.1 (C=O) ppm.

EXAMPLE 2 a) 175 g of the compound described in Example 1 and 96.6 g of potassium carbonate were presented in 950 ml of DMF. A mixture of 81.9 g of mercaptoethanol and 220 ml of DMF was added dropwise at from 60 to 65° C. The reaction mixture was then stirred at that temperature until the reaction had ended (TLC).

After cooling, the reaction mixture was diluted with 20% strength by weight aqueous sodium chloride solution and repeatedly extracted with ethyl acetate. Removing the solvent under reduced pressure left 175 g of the compound of the formula

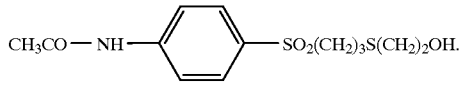

b) The compound described under a) was dissolved in 500 ml of water. Following the addition of 0.5 g of tungstic acid, 342 g of 30% strength by weight aqueous hydrogen peroxide solution were added dropwise at from 20 to 25° C. The reaction mixture was heated at 70° C. for 2 h. After the reaction had ended (TLC), the resulting precipitate was filtered off with suction at 10° C., washed with water and dried at about 30° C. under reduced pressure to leave 122 g of the compound of the formula

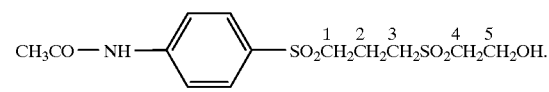

$^1$H-NMR (D$_6$-DMSO): δ=2.0 (m, 2H, 2-H)

2.1 (s, 3H, CH$_3$)

3.2 (m, 4H, 4-H, 5-H)

3.4 (t, 2H, 3-H)

3.8 (t, 2H, 1-H)

7.8 (brs, 4H, aromatic H)

11.3 (s, 1H, NH) ppm.

$^{13}$C-NMR (D$_6$-DMSO): δ=15.8 (C-2)

24.1 (CH$_3$)

51.7 (C-3)

53.4 (C-1)

55.0, 55.2 (C-4, C-5 )

118.8, 128.9, 132.0, 144.1 (aromatic C)

169.1 (C=O) ppm.

EXAMPLE 3

50 g of the compound described in Example 2b were heated for 8 h at from 80 to 85° C. in 500 g of half-concentrated hydrochloric acid. The reaction solution was subsequently concentrated at 50° C. under reduced pressure to leave 50 g of the compound of the formula

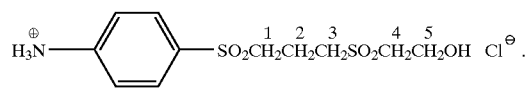

$^1$H-NMR (D$_6$-DMSO): δ=2.0 (m, 2H, 2-H)

3.3 (m, 6H, 3-H, 4-H, 5-H)

3.8 (t, 2H, 1-H)

6.9 (d, 2H, aromatic H)

7.2 (brs, 3H, NH$_3{}^\oplus$)

7.6 (d, 2H, aromatic H) ppm.

EXAMPLE 4

172.4 g of 1-bromo-3-chloropropane were added dropwise at from 20 to 25° C. to a mixture of 186.3 g of 3-nitrobenzenesulfinic acid, 500 ml of DMF and 151.4 g of potassium carbonate. The mixture was subsequently stirred at from 20 to 25° C. for 16 h. It was then diluted with water and repeatedly extracted with ethyl acetate. Removing the solvent under reduced pressure left 165 g of a compound of the formula

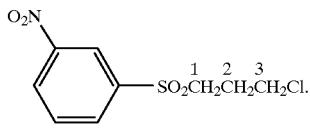

$^1$H-NMR (D$_6$-DMSO): δ=2.05 (m, 2H, 2-H)
3.6 (t, 2H, 3-H)
3.7 (t, 2H, 1-H)
8.0 (t, 1H, aromatic H)
8.4 (d, 1H, aromatic H)
8.6 (m, 2H, aromatic H) ppm.

EXAMPLE 5 a) 162.6 g of the compound described in Example 4 were reacted with 94.3 g of potassium carbonate and 53.6 g of thioethanol in 650 ml of DMF in the manner of Example 2a to yield 145.2 g of the compound of the formula

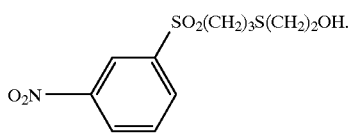

b) The compound described under a) was then oxidized with 256 g of 30% strength by weight aqueous hydrogen peroxide solution in 120 ml of water in the manner of Example 2b. Drying the isolated product left 124 g of the compound of the formula

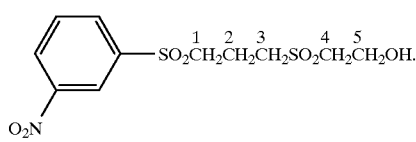

$^1$H-NMR (D$_6$-DMSO): δ=20 (m, 2H, 2-H)
3.2 (m, 4H, 4-H, 5-H)
3.7 (t, 2H, 3-H)
3.8 (t, 2H, 1-H)
8.0 (t, 1H, aromatic H)
8.4 (t, 1H, aromatic H)
8.6 (m, 2H, aromatic H) ppm.
$^{13}$C-NMR (D$_6$-DMSO): δ=15.5 (C-2)
51.7 (C-1)
52.9 (C-3)
55.0, 55.2 (C-4, C-5)
122.7, 128.5, 131.6, 133.8
140.3, 148.1 (aromatic C)

EXAMPLE 6

33.7 g of the compound described in Example 5b) were dissolved in 300 g of methanol and 2 g of propionic acid. 5 g of Raney nickel were added for a hydrogenation at 40° C. under a hydrogen pressure of 2 bar. After the uptake of hydrogen had ceased, the catalyst was filtered off and the filtrate was freed of solvent to leave 30.0 g of the compound of the formula

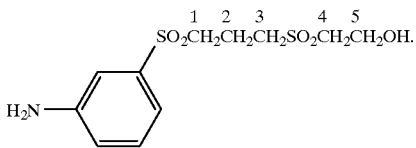

$^1$H-NMR (D$_6$-DMSO): δ=1.8 (m, 2H, 2-H)
3.1–3.7 (m, 8H, 1-, 3-, 4- and 5-H)
4.3 (m, 1H, OH)
5.7 (brs, 2H, NH$_2$)
6.8–7.3 (t, 4H, aromatic H)

EXAMPLE 7

Example 1 was repeated with 188 g of 1-bromo-4-chlorobutane, affording 262 g of the compound of the formula

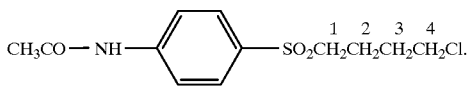

$^1$H-NMR (D$_6$-DMSO): δ=1.5–1.9 (m, 4H, 2-, 3-H)
2.1 (s, 3H, CH$_3$)
3.3 (t, 2H, 4-H)
3.6 (t, 2H, 1-H)
7.8 (brs, 4H, aromatic H)
10.4 (s, 1H, NH) ppm.

EXAMPLE 8

184 g of the compound described in Example 7 were reacted with 81 g of mercaptoethanol in the manner of Example 2a) and the product then oxidized in the manner of Example 2b), affording 202 g of the compound of the formula

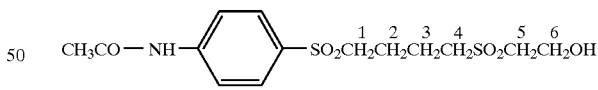

$^1$H-NMR (D$_6$-DMSO): δ=1.6–1.9 (m, 4H, 2-, 3-H)
2.1 (s, 3H, CH$_3$)
3.1 (m, 4H, 5-, 6-H)
3.3 (m, 2H, 4-H)
3.8 (t, 2H, 1-H)
7.8 (brs, 4H, aromatic H)
10.4 (s, 1H, NH) ppm.

EXAMPLE 9

Example 1 was repeated with 227 g of 4-(2-acetylaminoethyl)benzenesulfinic acid, affording 258 g of a compound of the formula

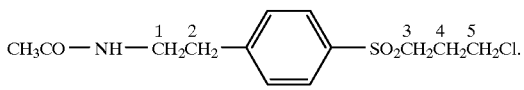

$^1$H-NMR (D$_6$-DMSO): δ=1.8 (s, 3H, CH$_3$)
2.0 (q, 2H, 4-H)
2.8 (t, 2H, 2-H)
3.3 (t, 2H, 5-H)
3.4 (m, 2H, 1-H)
3.7 (t, 2H, 3-H)
7.5 (d, 2H, aromatic H)
7.8 (d, 2H, aromatic H)
8.0 (brs, 1H, NH).

EXAMPLE 10

Example 2 was repeated with 192 g of the compound described in Example 9, affording (on drying under reduced pressure) 185 g of the compound of the formula

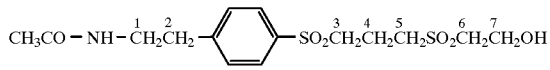

$^1$H-NMR (D6-DMSO): δ=1.8 (s, 3H, CH$_3$)
2.0 (m, 2H, 4-H)
2.9, 3.2–3.6 (m, in total 10H,
1-, 2-, 5-, 6- and 7-H)
3.8 (t, 2H, 3-H)
7.5 (d, 2H, aromatic H)
7.8 (d, 2H, aromatic H)
8.0 (brs, 1H, NH) ppm.

EXAMPLE 11

50 g of the compound described in Example 2b were introduced into 150 g of 100 % strength by weight sulfuric acid at from 35 to 40° C. with ice cooling and the mixture was stirred at room temperature for 12 h.

After the reaction had ended (TLC), the reaction mixture was poured onto 450 g of ice and the resulting mixture was adjusted to pH 5 by sprinkling with sodium carbonate while stirring and cooling.

The result obtained was an electrolyte-containing solution of the compound of the formula

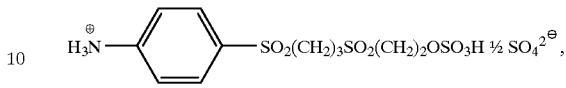

which can be used for subsequent reactions, in particular dye syntheses, without further purification.

EXAMPLE 12

50 g of the compound described in Example 2b were introduced into 150 g of 24% strength by weight oleum at from 35 to 40° C. with ice cooling and the mixture was stirred at 85° C. for 6 h.

After the reaction had ended (TLC), the reaction mixture was poured onto 450 g of ice and the resulting mixture was adjusted to pH 5 by sprinkling with sodium carbonate while stirring and cooling.

After cooling down to 0–5° C., the mixture was stirred at that temperature for 1 h, and the precipitated sodium sulfate was then filtered off.

The result obtained was an electrolyte-containing solution of the compound of the formula

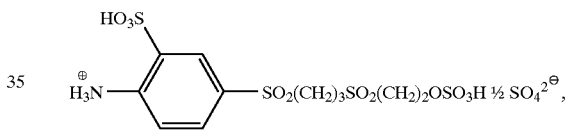

which can be used for subsequent reactions, in particular dye syntheses, without further purification.

The same method affords the compounds listed in the table which follows.

$$R^2-\underset{\underset{R^3}{|}}{\overset{\overset{R^1}{|}}{Ar}}-SO_2-E-SO_2CH_2CH_2Q$$

| Ex. No. | $R^2-\underset{\underset{R^3}{|}}{\overset{\overset{R^1}{|}}{Ar}}$ | E | Q |
|---|---|---|---|
| 13 | H$_2$N—⟨phenyl, meta⟩ | CH$_2$CH$_2$CH$_2$ | OSO$_3$H |
| 14 | H$_2$N—⟨phenyl with HO$_3$S⟩ | CH$_2$CH$_2$CH$_2$ | OSO$_3$H |

-continued
$$R^2 - \underset{\underset{R^3}{|}}{\overset{\overset{R^1}{|}}{Ar}} - SO_2 - E - SO_2CH_2CH_2Q$$
| Ex. No. | $R^2-\underset{\underset{R^3}{|}}{\overset{\overset{R^1}{|}}{Ar}}$ | E | Q |
|---|---|---|---|
| 15 | 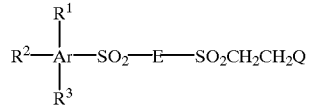 | CH₂CH₂CH₂CH₂ | OSO₃H |
| 16 | 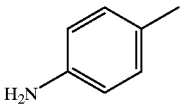 | CH₂CH₂CH₂ | OSO₃H |
| 17 | 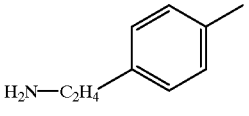 | CH₂CH₂CH₂ | OSO₃H |
| 18 | 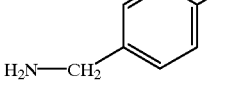 | CH₂CH₂CH₂ | OSO₃H |
| 19 | 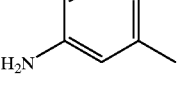 | CH₂CH₂CH₂ | OSO₃H |
| 20 | 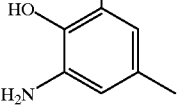 | CH₂CH₂CH₂ | OSO₃H |
| 21 | 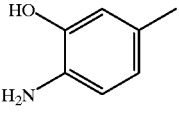 | CH₂CH₂CH₂ | OSO₃H |
| 22 | 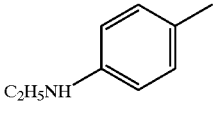 | CH₂CH₂CH₂CH₂ | OSO₃H |
| 23 | 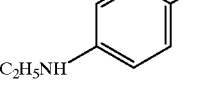 | CH₂CH₂CH₂ | OSO₃H |
| 24 | 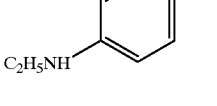 | CH₂CH₂CH₂ | OSO₃H |

-continued $$R^2-\underset{\underset{R^3}{\overset{R^1}{|}}}{Ar}-SO_2-E-SO_2CH_2CH_2Q$$

| Ex. No. | $R^2-\underset{\underset{R^3}{\overset{R^1}{|}}}{Ar}$ | E | Q |
|---|---|---|---|
| 25 | 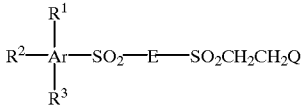 6-amino-2-methylnaphthalene | $CH_2CH_2CH_2$ | $OSO_3H$ |
| 26 | 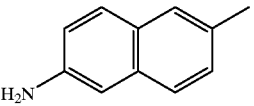 2-amino-6-methyl-1-naphthalenesulfonic acid | $CH_2CH_2CH_2$ | $OSO_3H$ |
| 27 | 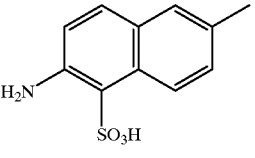 6-amino-2-methylnaphthalene | $CH_2CH_2CH_2CH_2$ | $OSO_3H$ |
| 28 | 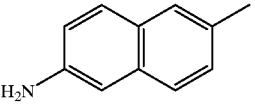 4-amino-2-methyl-1-chlorobenzene | $CH_2CH_2CH_2$ | OH |
| 29 | 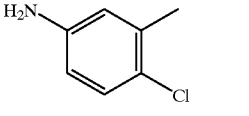 4-amino-2-methyl-1-(NH(CH$_2$)$_2$OSO$_3$H)benzene | $CH_2CH_2CH_2$ | $OSO_3H$ |

We claim:

1. Sulfonyl compounds of the formula I $$R^2-\underset{\underset{R^3}{\overset{R^1}{|}}}{Ar}-SO_2-E-S(O)_n-Y, \quad (I)$$

where
n is 0, 1 or 2,
Y is vinyl or a radical of the formula $C_2H_4Q$, where Q is an alkali-detachable group,
E is $C_3$–$C_6$-alkylene with or without interruption by 1 or 2 oxygen atoms in ether function,
Ar is the radical of benzene or naphthalene, and
$R^1$, $R^2$ and $R^3$ are independently of each other hydrogen, $C_1$–$C_6$-alkyl with or without amino or $C_1$–$C_4$-alkanoylamino substitution, $C_1$–$C_6$-alkoxy, hydroxyl, halogen, nitro, amino, $C_1$–$C_4$-alkanoylamino, mono- or di($C_1$–$C_6$-alkyl)amino, hydroxysulfonyl, carboxyl, carbamoyl, mono- or di($C_1$–$C_6$-alkyl)carbamoyl, sulfamoyl, mono- or di($C_1$–$C_6$-alkyl)sulfamoyl, cyano or a radical of the formula $(NH-)_m(CH_2-)_qSO_2-Y$, where m is 0 or 1, q is 0, 2 or 3, and Y is as defined above.

2. Sulfonyl compounds as claimed in claim 1 wherein n is 0 or 2.

3. Sulfonyl compounds as claimed in claim 1 wherein E is $C_3$- or $CH_4$-alkylene.

4. Sulfonyl compounds as claimed in claim 1 wherein Ar is the radical of benzene.

5. Sulfonyl compounds as claimed in claim 1 wherein $R^1$ is $C_1$–$C_4$-alkyl with or without amino or $C_1$–$C_4$-alkanoylamino substitution, nitro, amino or $C_1$–$C_4$-alkanoylamino and $R^2$ and $R^3$ are independently of each other hydrogen, $C_1$–$C_4$-alkoxy, hydroxyl, halogen, hydroxysulfonyl or carboxyl.

6. Sulfonyl compounds as claimed in claim 1, wherein said group Q is chlorine, bromine, $C_1$–$C_4$ alkylsulfonyl, phenylsulfonyl, $OS_3H$, $SSO_3H$, $OP(O)(OH)_2$, $C_1$–$C_4$-alkylsulfonyloxy, phenylsulfonyloxy, $C_1$–$C_4$-alkanoyloxy, di($C_1$–$C_4$-alkyl)amino or a radical of the formula

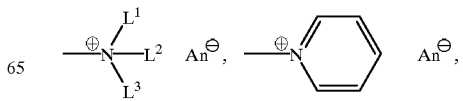

-continued

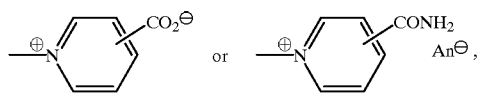 or 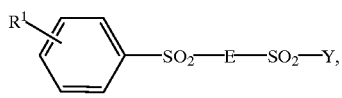

where $L^1$, $L^2$ and $L^3$ are independently of each other $C_1$–$C_4$-alkyl or benzyl and $An^\ominus$ is an equivalent of an anion, wherein said anion is fluoride, chloride, bromide, iodide, mono-, di- or trichloroacetate, methanesulfonate, benzenesulfonate and 2- or 4-methylbenzenesulfonate.

7. Sulfonyl compounds as claimed in claim 1, wherein bridging group E is $(CH_2)_3$, $(CH_2)_4$, $(CH_2)_5$, $(CH_2)_6$, $CH(CH_3)CH_2$, $CH(CH_3)CH(CH_3)$, $(CH_2)_2O(CH_2)_2$, $(CH_2)_2O(CH_2)_3$, $(CH_2)_3O(CH_2)_3$ or $(CH_2)_2O(CH_2)_2O(CH_2)_2$.

8. A sulfonyl compound of the formula:

$$R^1-\text{C}_6\text{H}_4-SO_2-E-SO_2-Y \qquad (Ia)$$

wherein
Y is vinyl, 2-sulfatoethyl, 2-chloroethyl or 2-acetyloxyethyl;
E is $C_3$–$C_4$-alkylene and
$R^1$ is a $C_1$–$C_4$ alkyl optionally substituted by amino or $C_1$- or $C_2$-alkanoylamino; nitro, amino or $C_1$–$C_2$-alkanoylamino.

* * * * *